United States Patent
Jo et al.

(10) Patent No.: US 9,107,568 B2
(45) Date of Patent: Aug. 18, 2015

(54) CAPSULE TYPE ENDOSCOPE AND METHOD FOR FABRICATING THE SAME

(75) Inventors: Wan-Hee Jo, Chungcheongbuk-do (KR); Jang-Sik Moon, Chungcheongbuk-do (KR)

(73) Assignee: Intellectual Ventures II LLC, Wilmington, DE (US)

( * ) Notice: Subject to any disclaimer, the term of this patent is extended or adjusted under 35 U.S.C. 154(b) by 2202 days.

(21) Appl. No.: 11/453,820

(22) Filed: Jun. 16, 2006

(65) Prior Publication Data

US 2006/0287580 A1    Dec. 21, 2006

(30) Foreign Application Priority Data

Jun. 17, 2005  (KR) .................. 10-2005-0052337
May 17, 2006  (KR) .................. 10-2006-0044166

(51) Int. Cl.
| | |
|---|---|
| *A61B 1/04* | (2006.01) |
| *A61B 1/00* | (2006.01) |
| *A61B 1/06* | (2006.01) |
| *H04N 5/225* | (2006.01) |
| *H04N 5/235* | (2006.01) |
| *H04N 5/361* | (2011.01) |

(52) U.S. Cl.
CPC ......... *A61B 1/00009* (2013.01); *A61B 1/00036* (2013.01); *A61B 1/041* (2013.01); *H04N 5/2256* (2013.01); *H04N 5/2354* (2013.01); *H04N 5/361* (2013.01); *H04N 2005/2255* (2013.01)

(58) Field of Classification Search
CPC ................... A61B 1/00009; A61B 1/00036
USPC ......... 600/101, 109, 118, 160, 178, 180, 181, 600/473, 475–477; 348/65, 68, 73, 74, 241, 348/243
See application file for complete search history.

(56) References Cited

U.S. PATENT DOCUMENTS

| | | | | | |
|---|---|---|---|---|---|
| 4,145,043 | A | * | 3/1979 | Olliges ........................... | 463/31 |
| 4,646,724 | A | * | 3/1987 | Sato et al. ..................... | 600/109 |
| 5,172,225 | A | * | 12/1992 | Takahashi ........................ | 348/74 |
| 6,641,529 | B2 | * | 11/2003 | Kuranishi ..................... | 600/160 |
| 7,008,374 | B2 | * | 3/2006 | Hakamata ..................... | 600/109 |

(Continued)

FOREIGN PATENT DOCUMENTS

| | | |
|---|---|---|
| JP | 2001-224553 | 8/2001 |
| JP | 2005-150744 | 6/2005 |
| KR | 2004-44232 | 5/2004 |

*Primary Examiner* — Anhtuan T Nguyen
*Assistant Examiner* — Rynae Boler
(74) *Attorney, Agent, or Firm* — McAndrews, Held & Malloy, Ltd.

(57) ABSTRACT

An image sensing system includes: a light emitting device; a pixel configured to capture an optical signal and to convert the optical signal into an analog image signal; an analog circuit configured to selectively filter the analog image signal; an analog-to-digital converting circuit configured to convert the analog image signal to a digital image signal; a digital circuit configured to receive the digital image signal and to switch the light emitting device on and off; wherein the digital image signal includes a dark image frame if the optical signal is captured when the light emitting device is off; wherein the digital image signal includes an effective image frame if the optical signal is captured when the light emitting device is on and the analog circuit is configured to filter the analog image signal; and wherein the digital image signal includes a punctured image frame if the optical signal is captured when the light emitting device is on and the analog circuit is not configured to filter the analog image signal.

17 Claims, 2 Drawing Sheets

(56) References Cited

U.S. PATENT DOCUMENTS

| | | | |
|---|---|---|---|
| 7,616,238 B2* | 11/2009 | Avni et al. | 348/243 |
| 7,630,754 B2* | 12/2009 | Mori et al. | 600/476 |
| 2001/0052941 A1* | 12/2001 | Matsunaga et al. | 348/308 |
| 2002/0158976 A1* | 10/2002 | Vni et al. | 348/243 |
| 2003/0156667 A1* | 8/2003 | Nishio | 375/345 |
| 2004/0212703 A1* | 10/2004 | Sugimoto et al. | 348/241 |
| 2004/0246858 A1* | 12/2004 | Saigusa et al. | 369/53.31 |
| 2005/0231633 A1 | 10/2005 | Yuyama et al. | 348/370 |
| 2005/0270372 A1* | 12/2005 | Henninger | 348/143 |
| 2006/0036131 A1* | 2/2006 | Glukhovsky et al. | 600/160 |
| 2006/0098107 A1* | 5/2006 | Lee et al. | 348/241 |
| 2006/0184039 A1* | 8/2006 | Avni et al. | 600/476 |

* cited by examiner

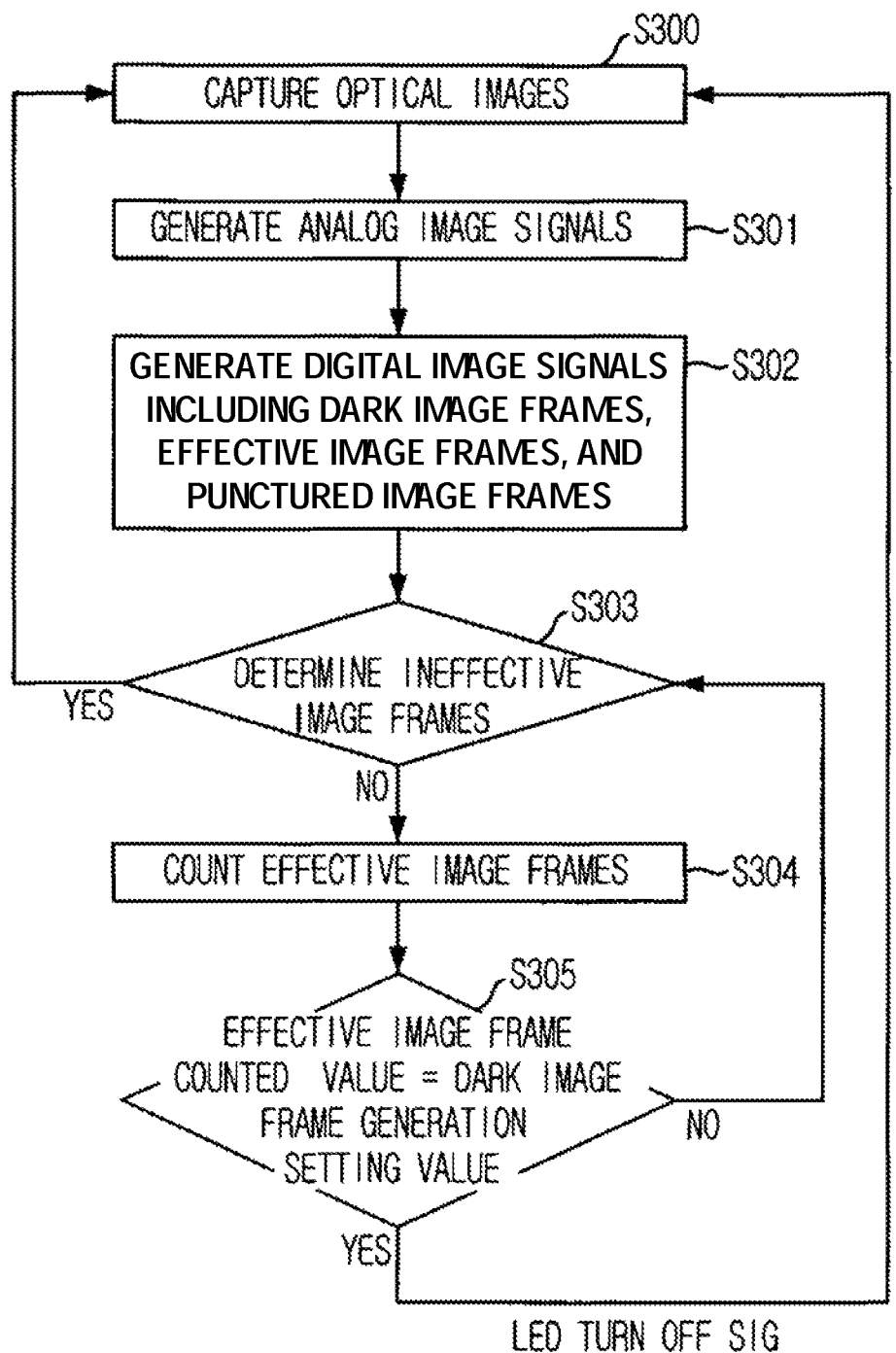

CAPSULE TYPE ENDOSCOPE AND METHOD FOR FABRICATING THE SAME

FIELD OF THE INVENTION

The present invention relates to a technology of capturing images inside a human body, and more particularly to an image sensor for a capsule type endoscope.

DESCRIPTION OF RELATED ARTS

An endoscope, which is a representative one among a variety of apparatuses for capturing images for body's internal structure, is used for providing upper and lower images of a stomach or intestines. Thus, the endoscope is widely used in a field of medicine recently.

A capsule type endoscope, which has been newly developed since 2000 is a capsule type subminiature endoscope enabling a doctor to directly examine the intestines or an internal structure of a coelom through a video screen or a computer monitor, when a patient swallows the capsule endoscope like a pill.

Many patients prefer taking medication to the endoscopic examination because a typical endoscope brings about pain, indisposition, etc. during the examination. Therefore, the capsule type endoscope has been introduced to overcome the above disadvantages of the typical endoscope. In particular, the capsule endoscope has been developed in order that it may be used for diagnosing disease in the small intestine which is the longest internal organ among gastrointestinal systems.

The capsule type endoscope operates in a human body having a predetermined temperature. Hence, a current is generated by the temperature of the human body even when the light does not completely lighten an image sensor of the capsule type endoscope. This current is called a dark current. If the dark current is generated, the image sensor has not only electrical signals caused by optical factors but also other electrical signals. Accordingly, in case that the light does not lighten, a noise including a predetermined signal level may occur. This noise is called a black level.

Typically, a peripheral region of a photodevice is covered by using a metal shielded pixel layer to form an optical black pixel region. An average value of the black level is obtained through an image sensor under a state which the light is turned off (i.e., under an aphotic state) in the optical black pixel region. The average value of the black level is offset from effective image data captured in a photic state. The black level may be reduced as described above.

However, the metal shielded pixel layer increases an area of the image sensor and as a result, a size of the capsule type endoscope and a production cost thereof may be increased.

A dark noise may be generated by the dark current. An impurity or another material may be added into an interface between a photo device and a device isolation layer so as not to generate the dark current and to settle down the dark noise. However, the added impurity or material may also increase the size of the capsule type endoscope.

The black level is settled down in an analog circuit and a digital circuit inside the capsule type endoscope and thus, electrical power is wasted.

SUMMARY OF THE INVENTION

It is, therefore, a primary object of the present invention to provide a light emitting device (LED) control circuit of an image sensor capable of generating control signals to control a light emitting device inside the image sensor to make an aphotic state inside the image sensor, and a method thereof.

It is, another object of the present invention to provide a light emitting device control circuit of an image sensor capable of performing compensation with respect to a black level and a dark noise of image data out of a human body through software, and a method thereof.

It is, still another object of the present invention to provide a light emitting device control circuit of an image sensor capable of saving power consumption and a method thereof.

In accordance with one aspect of the present invention, there is provided an image sensor for a capsule type endoscope in which images are processed by a frame unit, including: a control unit configured to generate a control signal to turn off a light emitting device installed out of the image sensor in every periodical frame among a plurality of frames.

In accordance with another aspect of the present invention, there is provided a capsule type endoscope system, including: an image sensor including a control unit for generating a control signal to turn off a light emitting device in every periodical frame among a plurality of frames; the light emitting device controlled in response to the control signal generated by the control unit; and an image data compensation unit to compensate image data which are output signals of the image sensor.

In accordance with still another aspect of the present invention, there is provided a method for controlling a light emitting device of an image sensor in which images are processed by a frame unit, including: counting frames; comparing a counted value with a light emitting device control signal generation setting value; and generating a light emitting device control signal if the counted value is identical with the light emitting device control signal generation setting value.

BRIEF DESCRIPTION OF THE DRAWINGS

The above and other objects and features of the present invention will become better understood with respect to the following description of the exemplary embodiments given in conjunction with the accompanying drawings, in which:

FIG. 2 describes a flow chart of a method for controlling a light emitting device in accordance with an embodiment of the present invention.

DETAILED DESCRIPTION OF THE INVENTION

Figure 1:
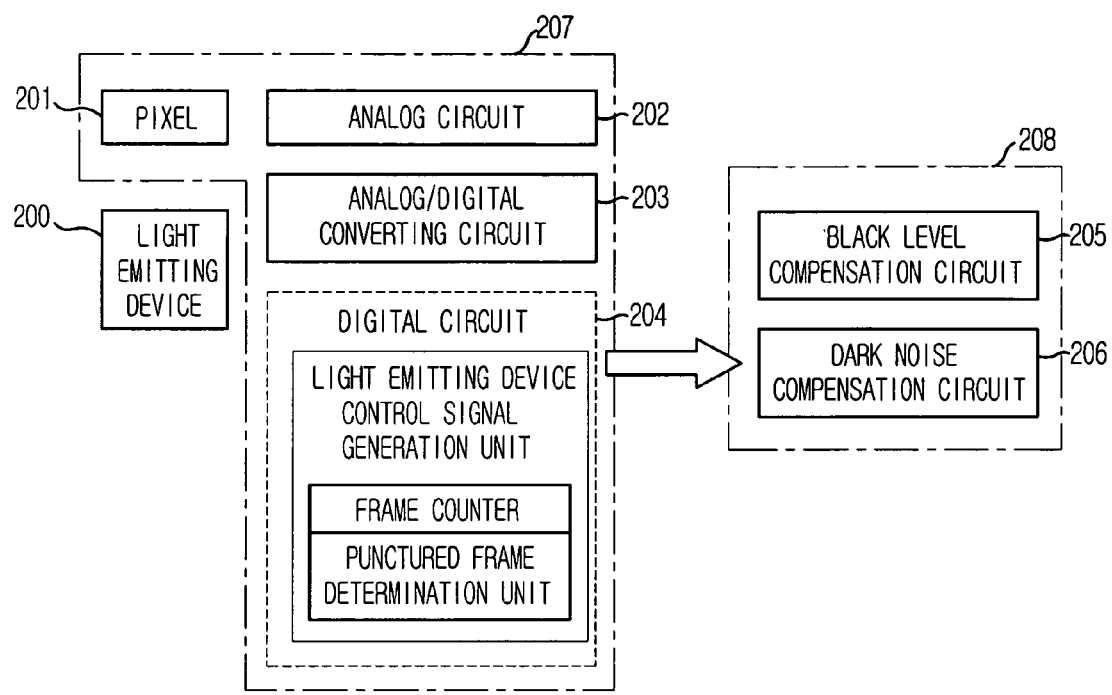
FIG. 1 illustrates a block diagram of a capsule type endoscope and an image data compensation circuit receiving and processing output signals of the capsule type endoscope.

Hereinafter, detailed descriptions on certain embodiments of the present invention will be provided with reference to the accompanying drawings.

FIG. 1 illustrates a block diagram of a capsule type endoscope and an image data compensation circuit receiving output signals of the capsule type endoscope and processing the output signals in accordance with an embodiment of the present invention.

The capsule type endoscope includes an image sensor 207 capturing an image of a diseased part of a human body and transferring the captured image out of the human body, and a light emitting device 200 lightening the diseased part.

An image data compensation circuit 208 includes a black level compensation circuit 205 compensating a black level, and a dark noise compensation circuit 206 compensating a dark noise.

The image sensor 207 includes a pixel 201, an analog circuit 202, an analog/digital converting circuit 203, and a digital circuit 204. The pixel 201 converts an optically captured image into electrical analog image signals. The analog circuit 202 removes a noise such as a fixed pattern noise (FPN) by filtering the analog image signals outputted from the pixel 201. The analog/digital converting circuit 203, which is included in the analog circuit 202, converts the analog image signals into digital image signals. The digital circuit 204 includes a light emitting device control signal generation unit to control the light emitting device 200, and processes and transfers the digital image signals out of the human body.

The light emitting device control signal generation unit includes a frame counter counting an individual output frame of the image sensor 207, and a punctured frame determination unit to determine whether the frames are punctured or not for low power consumption.

The image data compensation circuit 208 includes a black level compensation circuit 205 and a dark noise compensation circuit 206. The black level compensation circuit 205 compensates a black level with respect to the digital image signals which are image frames transferred from the digital circuit 204. The digital image signals include effective image frames generated by being captured in a photic state, dark image frames captured in an aphotic state, and punctured frames generated for low power consumption. The dark noise compensation circuit 206 compensates a dark noise with respect to the digital image signals transferred from the digital circuit 204.

In more detail of an operation of the capsule type endoscope including the light emitting device 200 and the image sensor 207, and the image data compensation circuit 208, the analog image signals generated in the pixel 201 by receiving the light from the light emitting device 200 removes a noise and then, are converted to the digital image signals which are the frames generated in the photic state (hereinafter referred to as effective image frames). The effective image frames are transferred to the image data compensation circuit 208.

In contrast to the effective image frames, the digital image signals which are the frames generated when the light emitting device 200 is turned off, i.e., in the aphotic state (hereinafter referred to as dark image frames) are generated in every desired period of the consecutive effective image frames. Thus, the dark image frames are transferred to the image data compensation circuit 208 along with the effective image frames.

Afterwards, an image data compensation is performed through the effective image frames and the dark image frames.

The black level is compensated by offsetting the dark image frames against the effective image frames. The dark image frames can be compared with the effective image frames through an average value of each unit pixel. Also, the dark image frames can be compared by each unit pixel. That is, the dark image frames can be individually compared with each other.

The dark noise is compensated by calculating an average value of the dark image frames by each unit pixel and offsetting the average value of the dark image frames against an average value of the effective image frames by each unit pixel.

As described above, the black level compensation and the dark noise compensation are performed through software. Accordingly, the black level compensation and the dark noise compensation can more easily respond to the image data compensation than those performed through a hardware which limitedly applies an algorithm for processing data on a real-time since a memory occupying a large area of the capsule endoscope cannot be used. Also, the black level compensation and the dark noise compensation make it possible to find out a unit pixel having a defect since the black level compensation and the dark noise compensation can cumulate the dark image frames by each unit pixel and thus, compare the dark image frames by each frame.

A method for controlling the light emitting device 200 to generate the dark image frames will be explained hereinafter.

FIG. 2 illustrates a flow chart of a method for controlling a light emitting device in accordance with an embodiment of the present invention.

The method for controlling the light emitting device includes the steps of generating optical image signals by capturing an image of a diseased part of a human body in a photic state at S300, converting the optical image signal to analog image signals at S301, converting the analog image signals to digital image signals (e.g., image frames) at S302, deciding whether the digital image signals are punctured or not at S303, counting the effective image frames when the digital image frames are punctured at S304, and generating light emitting device control signals LED TURN OFF SIG when a counted value is identical with a dark image frame generation setting value which is pre-set at S305.

The method for controlling the light emitting device is moved to the step of generating the optical image signals at S300 from the step of deciding whether the digital image signals are the puncture frames at S303 if the digital image signals are punctured. If the counted value is not identical with the dark image frame generation setting value, the method for controlling the light emitting device is moved to the step of deciding whether the digital image signals are punctured or not at S303. After performing up to the step of generating the light emitting device control signals LED TURN OFF SIG at S305, the method for controlling the light emitting device is moved to the initial step and consecutively outputs image frames.

In summary, if the effective image frames (except for the punctured frames) captured in a photic state are generated as many as the predetermined number, i.e., if the counted value of the effective image frames is identical with the dark image frame generation setting value, the dark image frames are generated in a state which the light emitting device is accordingly turned off.

As described above, since a metal shielded pixel layer is typically installed to compensate the black level and the dark noise in the capsule type endoscope, a size of the capsule type endoscope is increased and accordingly, electric power is wasted. However, according to this embodiment of the present invention, the dark image frames generated by being captured in an aphotic state and the effective image frames generated by being captured in a photic state are used as software out of a human body (i.e., out of the capsule type endoscope) to compensate the black level and the dark noise. Accordingly, the aforementioned limitations can be settled down.

The punctured frames are generated among a plurality of frames by capturing the images in a state which the analog circuit is selectively turned off to reduce power consumption.

As described above, according to this embodiment of the present invention, an additional layer such as a metal shielded pixel layer is not formed in the image sensor for the capsule type endoscope and thus, a size of the image sensor for the capsule type endoscope can be reduced. Since a circuit controlling the light emitting device is installed in the image sensor for the capsule type endoscope, an additional circuit is not necessary. Also, circuits to compensate the black level and the dark noise are installed out of the capsule type endoscope and thus, the size of the image sensor for the capsule type endoscope can be reduced and electrical power can be saved.

The black level compensation and the dark noise compensation are processed through software. Accordingly, information of image data throughout various frames can be saved, calculated and processed. It is possible to easily increase efficiency in the compensation.

The present application contains subject matter related to the Korean patent application Nos. KR 2005-0052337 and KR 2006-0044166 respectively filed in the Korean Patent Office on Jun. 17, 2005 and May 17, 2006, the entire contents of which being incorporated herein by reference.

While the present invention has been described with respect to certain preferred embodiments, it will be apparent to those skilled in the art that various changes and modifications may be made without departing from the spirit and scope of the invention as defined in the following claims.

What is claimed is:

1. A capsule-type endoscope for use in a human body, wherein the capsule-type endoscope comprises:
    a light-emitting device configured to be:
        turned on during capture of an effective image frame and a punctured image frame; and
        turned off to create an aphotic state during capture of a dark image frame;
    a plurality of pixels configured to capture light and to convert the light into an analog image signal;
    an analog circuit configured to filter the analog image signal and configured to be:
        turned on during capture of the dark image frame and the effective image frame; and
        turned off during capture of the punctured image frame;
    an analog-to-digital converting circuit configured to convert the analog image signal into a digital image signal; and
    a digital circuit configured to receive the digital image signal and to switch the light-emitting device on and off;
    wherein the analog image signal includes information corresponding to each of the plurality of pixels; and
    wherein the digital image signal includes information corresponding to each of the plurality of pixels.

2. The capsule-type endoscope of claim 1, further comprising an image data compensation circuit.

3. The capsule-type endoscope of claim 2, wherein the image data compensation circuit comprises:
    a black level compensation unit; and
    a dark noise compensation unit.

4. The capsule-type endoscope of claim 2, further comprising:
    a capsule containing the light-emitting device, the plurality of pixels, the analog circuit, and the digital circuit;
    wherein the image data compensation circuit is outside of the capsule.

5. The capsule-type endoscope of claim 3, wherein the black level compensation unit is configured to offset pixel information in the digital image signal of the effective image frame by an average value of pixel information in the digital image signal of the dark image frame.

6. The capsule-type endoscope of claim 1, wherein the analog circuit is further configured to remove a fixed pattern noise from the analog image signal.

7. A method for sensing an image, the method comprising:
    turning an analog circuit on and off to selectively filter image data by filtering electrical analog image signals received from a pixel;
    generating a dark image frame by capturing image data in an aphotic state;
    generating an effective image frame by capturing image data in a photic state and by filtering the image data when the analog circuit is turned on; and
    generating a punctured image frame by capturing image data in the photic state when the analog circuit is turned off.

8. The method of claim 7, further comprising controlling a light-emitting device to cause the aphotic state and the photic state.

9. The method of claim 8, further comprising:
    counting the effective image frame to determine a counted value; and
    turning off the light-emitting device if the counted value equals a dark image frame generation setting value.

10. The method of claim 7, further comprising transferring out of a human body the dark image frame, the effective image frame, and the punctured image frame to an image data compensation circuit.

11. The method of claim 7, further comprising compensating for a black level by offsetting pixel information of the effective image frame by an average value of pixel information of the dark image frame.

12. The method of claim 7, further comprising converting, with an analog-to-digital converter, the image data selectively filtered by the analog circuit to form one of the dark image frame, the effective image frame, or the punctured image frame.

13. An image sensing system comprising:
    a light-emitting device configured to be:
        turned on during capture of an effective image frame and a punctured image frame; and
        turned off during capture of a dark image frame;
    a plurality of pixels configured to capture light and to convert the light into an analog image signal;
    an analog circuit configured to filter the analog image signal and configured to be:
        turned on during capture of the dark image frame and the effective image frame; and
        turned off during capture of the punctured image frame;
    an analog-to-digital converting circuit configured to convert the analog image signal into a digital image signal;
    a digital circuit configured to receive the digital image signal and to switch the light-emitting device on and off; and
    an endoscopic capsule encapsulating the light-emitting device, the plurality of pixels, the analog circuit, the analog-to-digital converting circuit, and the digital circuit;
    wherein the analog image signal includes information corresponding to each of the plurality of pixels; and
    wherein the digital image signal includes information corresponding to each of the plurality of pixels.

14. The image sensing system of claim 13, further comprising an image data compensation circuit outside of the endoscopic capsule.

15. The image sensing system of claim 14, wherein the image data compensation circuit comprises:
    a black level compensation unit; and
    a dark noise compensation unit.

16. The image sensing system of claim 15, wherein the black level compensation unit is configured to offset pixel information in the digital image signal of the effective image frame by an average value of pixel information in the digital image signal of the dark image frame.

17. The image sensing system of claim 13, wherein the analog circuit is further configured to remove a fixed pattern noise from the analog image signal.

* * * * *